United States Patent [19]
Martin et al.

[11] Patent Number: 4,661,365 [?]
[45] Date of Patent: Apr. 28, 1987

[54] SYNERGISTIC BIOCIDE OF DODECYL GUANIDINE HYDROCHLORIDE AND A MIXTURE OF 5-CHLORO-2-METHYL-4-ISOTHIAZOLIN-3-ONE

[75] Inventors: Cynthia H. Martin, Plainfield; Thomas M. LaMarre, Aurora, both of Ill.

[73] Assignee: Nalco Chemical Company, Naperville, Ill.

[21] Appl. No.: 874,925

[22] Filed: Jun. 16, 1986

[51] Int. Cl.$^4$ ............... A01N 37/52; A01N 43/80
[52] U.S. Cl. ................... 514/372; 210/764; 514/634
[58] Field of Search .................. 514/372, 634

[56] References Cited

U.S. PATENT DOCUMENTS

| | | | |
|---|---|---|---|
| 3,628,941 | 12/1971 | Marks | 514/634 |
| 3,929,561 | 12/1975 | Shema et al. | 514/372 |
| 4,499,071 | 2/1985 | Borovian | 514/372 |

OTHER PUBLICATIONS

Applied Microbiology, vol. 9, pp. 538–541, (1936) S. C. Kull et al., "Mixtures of Quaternary Ammonium Compounds and Long-Chain Fatty Acids as Antifungal Agents".

*Primary Examiner*—Allen J. Robinson
*Attorney, Agent, or Firm*—John G. Premo; Anthony L. Cupoli; Donald G. Epple

[57] ABSTRACT

A synergistic biocide blend of dodecyl guanidine hydrochloride with a mixture of 5-chloro-2-methyl-4-isothiazolin-3-one and 2-methyl-4-isothiazolin-3-one.

10 Claims, No Drawings

SYNERGISTIC BIOCIDE OF DODECYL GUANIDINE HYDROCHLORIDE AND A MIXTURE OF 5-CHLORO-2-METHYL-4-ISOTHIAZOLIN-3-ONE

FIELD OF THE INVENTION

The present invention relates to certain processes and compositions useful for inhibiting the growth of slime in water employed for industrial purposes, particularly water employed in the manufacture of pulp and paper, water employed in cooling water systems, as well as other industrial waters.

BACKGROUND

The mechanisms by which chemical agents exert antimicrobial activity depend upon the effective contact between the chemical and the organism, and involve disruptive interactions with some biochemical or physical component of the organism, which component is essential to its structure or metabolism. The targets may be an enzyme, or enzymes, the cell membrane, an intracellular system, the cytoplasm, or any combination of these. The nature of the action of the toxicant is dependent on the organism, on the antimicrobial agent, and on the environment in which the interaction occurs. The unique composition of each toxicant implies a different mode of action.

The present invention provides superior antimicrobial activity through a synergy in which the disruptive interaction on the organism by the two toxicants together is greater than the sum of both toxicants taken alone. The synergy does not arise from the expected activity of the components or from a predictable improvement in activity. In all cases, the synergism depends largely on the interactions of the antimicrobial agents with the organism. The cellular processes are so complex as to render such synergism an unpredictable, and indeed rare, phenomenon.

SUMMARY OF THE INVENTION

The novel compositions and methods of the present invention are processes or mixtures which show unexpected synergistic activity against bacteria and fungi which are common to industrial waters and which produce slimes in aqueous systems or bodies, which slimes are objectionable from either an operational or aesthetic point of view. Specifically, the invention is directed to the use of compositions comprising a combination of dodecyl quanidine hydrochloride (DGH) and a mixture of 5-chloro-2-methyl-4-isothiazolin-3-one and 2-methyl-4-isothiazolin-3-one (ISOTH). ISOTH is commercially available only in a 1.15 to 0.35 weight ratio of 5-chloro-2-methyl-4-isothiazolin-3-one to 2-methyl-4-isothiazolin-3-one, respectively.

The invention comprises a synergistic biocidal composition useful in treating industrial process waters to prevent and control the growth of gram-negative bacteria and fungi which comprises from 10–90% by weight of dodecyl guanidine hydrochloride and from 90–10% by weight of a mixture of 5-chloro-2-methyl-4-isothiazolin-3-one and 2-methyl-4-isothiazolin-3-one.

BACTERIA

The troublesome slimeforming bacteria in industrial process waters tend to be primarily gram-negative rod-shaped aerobes. Of this group, *Pseudomonas aeruginosa* is one of the most common and most difficult to control. The invention is capable of affording good control of *Pseudomonas aeruginosa*. It is also capable of affording control of other species of bacteria, in particular other species of gram-negative, rod-shaped aerobes of such genera as Aerobacter, Flavobacterium, Pseudomonas, for example, *Pseudomonas aeruginosa, Pseudomonas fluorescens, Pseudomonas levanicum, Pseudomonas stutzeri, Pseudomonas maltophilia, Aerobacter aerogenes, Aerobacter cloacae,* and others.

FUNGI

Similarly the fungi, *Aspergillus niger,* is one of the most common species of mold in process waters and one of the most difficult to control. *Saccharomyces cerevisiae* is a common yeast. This invention affords control of *Aspergillus niger* and *Saccharomyces cerevisiae* and other species of fungi which are common in process waters, species in such genera as Aspergillus, Monilia, as well as *Aspergillus fumigatus, Aspergillus niger, Penicillium chrysogenum, Monilia candida, Geotrichum candidum,* and *Saccharomyces cerevisiae.*

BIOCIDES

While the two biocides may be combined in the weight ratios shown above when they are combined to treat fungi and, in particular, either *Aspergillus niger* or *Saccharomyces cerevisiae,* they are particularly synergistic where the weight ratio of dodecyl guanidine hydrochloride to a mixture of 5-chloro-2-methyl-isothiazolin-3-one and 2-methyl-4-isothiazolin-3-one ranges between 90/10 to 10/90.

When the toxicants are combined to treat bacteria, in particular, gram-negative slimeforming aerobes, they are most highly synergistic where the weight percent of dodecyl guanidine hydrochloride ranges between 90–25% and the weight percent of the mixture of 5-chloro-2-methyl-4-isothiazolin-3-one and 2-methyl-4-isothiazolin-3-one ranges between 10–75%.

Dosages

For most industrial waters, an effective biocide dosage will be within the range of from 1–10 ppm as actives. The actual dosage used will depend on the water treated.

EVALUATION OF THE INVENTION

Test Procedure

The synergism of these components is demonstrated by adding dodecyl guanidine hydrochloride (DGH) and a mixture of 5-chloro-2-methyl-4-isothiazolin-3-one and 2-methyl-4-isothiazolin-3-one (ISOTH) in varying ratios over a range of concentrations to sterile white water from a paper mill. The white water, adjusted to the desired pH, was inoculated with *Pseudomonas aeruginosa,* ATCC 15442.

The total count of the control was $1.36 \times 10^8$ bacteria per milliliter. The concentrations of the above toxicants were added to aliquots of the inoculated white water, and these aliquots were incubated at 37° C. for 24 hours. In this study of the control of bacterial growth, the nutrient medium for plating was tryptone glucose extract agar, poured at 50° C. into sterile Petri dishes containing the appropriate dilutions of the white water which had been inoculated and treated as described. Once the medium in these dilution plates had solidified, the plates were inoculated for over forty-eight hours at 37° C. After the incubation, the results were read as growth or no growth; the lowest concentration of each toxicant or of each ratio of the combined toxicants that prevented growth on the agar was taken as the end point. This procedure provides the toxicant with a greater challenge by testing the toxicants under conditions which approximate the conditions under which they will be used.

The test against fungi followed the same procedure with these exceptions. The white water was inoculated with *Aspergillus niger* and *Saccharomyces cerevisiae* to a count of $1.0 \times 10^4$ molds and $1.5 \times 10^5$ yeasts per milliliter. The aliquots of inoculated and treated white water were incubated at 30° C. for 24 hours. The medium used for plating was potato dextrose agar, acidified with tartaric acid to a pH of 4.5. The plates were incubated for five days at 30° C.

The end points of each of the ratios tested were compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology*, Vol. 9, pages 538–541, (1936), which is herein included as reference.

As regards the Kull et al. document, the data here presented can be described as follows:

$Q_A$ = the ppm of actives of DGH alone which produced an endpoint $Q_a$ = the ppm of actives of DGH, in combination, which produced an endpoint $Q_B$ = the ppm of actives of ISOTH alone which produced and endpoint $Q_b$ = the ppm of actives of ISOTH, in combination, which produced an endpoint $$\text{if } \frac{Q_a}{Q_A} + \frac{Q_b}{Q_B} \begin{cases} < 1 \text{ indicates synergy} \\ > 1 \text{ indicates antagonism} \\ = 1 \text{ indicates additivity} \end{cases}$$

Ratios of DGH/ISOTH: 100/0, 0/100, 90/10, 10/90, 75/25, 25/75, 50/50.

Concentrations tested for each ratio in terms of parts per million of actives: 0.3, 0.6, 1.0, 1.5, 3.0, 5.0, 7.5, 10, 20, 30, 40, 50, 60.

The above test method is reproduceable and is a good method for determining the range of synergism existing against candidate biocides being screened for application in the treatment of biologically contaminated industrial waters. The efficacy and validity of this test method is discussed in the Appendix which appears hereafter. In order to present the following test results as clearly as possible, the Appendix also contains the calculations used to produce the test results set forth in Table I and II. The effectiveness of combinations of DGH and ISOTH are set forth below in Tables I and II.

TABLE I

Synergism Study For Combination Biocides Against Bacteria

Growth: +
No Growth: −
Control Culture: $1.36 \times 10^8$ organism per ml

| Ratio DGH/ ISOTH | .3 | .6 | 1.0 | 1.5 | 3.0 | 5.0 | 7.5 | 10 | 20 | 30 | 40 | 50 | 60 |
|---|---|---|---|---|---|---|---|---|---|---|---|---|---|
| 100/0 | + | + | + | + | + | + | + | + | + | + | + | − | − |
| 0/100 | + | + | + | + | + | − | − | − | − | − | − | − | − |
| 90/10 | + | + | + | + | + | + | + | − | − | − | − | − | − |
| 10/90 | + | + | + | + | + | − | − | − | − | − | − | − | − |
| 75/25 | + | + | + | + | + | + | − | − | − | − | − | − | − |

TABLE I-continued

Synergism Study For Combination Biocides Against Bacteria

| | | | | | | | | | | | | | |
|---|---|---|---|---|---|---|---|---|---|---|---|---|---|
| 25/75 | + | + | + | + | + | − | − | − | − | − | − | − | − |
| 50/50 | + | + | + | + | + | − | − | − | − | − | − | − | − |

| DGH/ISOTH Ratio | $\frac{Q_a}{Q_A} + \frac{Q_b}{Q_B}$ | Rating |
|---|---|---|
| 90/10 | 0.380 | < 1 Synergy |
| 10/90 | 0.910 | < 1 Synergy |
| 75/25 | 0.488 | < 1 Synergy |
| 25/75 | 0.775 | < 1 Synergy |
| 50/50 | 0.550 | < 1 Synergy |

TABLE II

SYNERGISM STUDY FOR COMBINATION BIOCIDES AGAINST FUNGI

Growth: +
No Growth: −
Control Culture: $1.5 \times 10^5$ molds/ml
$1.5 \times 10^5$ yeast/ml

| Ratio DGH/ ISOTH | 1 | 3 | 5 | 7.5 | 10 | 20 | 30 | 10 | 50 | 60 | 70 | 80 |
|---|---|---|---|---|---|---|---|---|---|---|---|---|
| 100/0 | + | + | + | + | + | + | + | − | − | − | − | − |
| 0/100 | + | + | + | − | − | − | − | − | − | − | − | − |
| 90/10 | + | + | + | + | − | − | − | − | − | − | − | − |
| 10/90 | + | + | − | − | − | − | − | − | − | − | − | − |
| 75/25 | + | + | + | − | − | − | − | − | − | − | − | − |
| 25/75 | + | + | − | − | − | − | − | − | − | − | − | − |
| 50/50 | + | − | − | − | − | − | − | − | − | − | − | − |

| Ratio DGH/ISOTH | $\frac{Q_a}{Q_A} + \frac{Q_b}{Q_B}$ | Rating |
|---|---|---|
| 90/100 | 0.358 | < 1 Synergy |
| 10/90 | 0.613 | < 1 Synergy |
| 75/25 | 0.391 | < 1 Synergy |
| 25/75 | 0.531 | < 1 Synergy |
| 50/50 | 0.238 | < 1 Synergy |

ANTAGONISTIC COMBINATIONS

The two components of the present invention were tested singly with a variety of other toxicants, using the methods described above; as is expected, most such combinations are antagonistic or merely additive. Two such examples are presented below in order to better show the nature of such testing.

First the mixture of 5-chloro-2-methyl-4-isothiazolin-3-one and 2-methyl-4-isothiazolin-3-one (ISOTH) was found to be antagonistic in combination with 1,5-pentanedial (PD) against bacteria.

| Ratio PD/ISOTH | Endpoint (ppm actives) | $\frac{Q_a}{Q_A} + \frac{Q_b}{Q_B}$ | Rating |
|---|---|---|---|
| 100/0 | 100 | 1.00 | |
| 0/100 | 3 | 1.00 | |
| 90/10 | 30 | 1.27 | Antagonistic |
| 10/90 | 20 | 1.82 | Antagonistic |
| 75/25 | 3 | 0.76 | Synergistic |
| 25/75 | 5 | 1.51 | Antagonistic |
| 50/50 | 10 | 1.72 | Antagonistic |

Second, dodecyl guanidine hydrochloride (DGH) was found to be antagonistic in combination with 2,2-dibromo-3-nitrilopropionamide (DBNPA), when tested against bacteria.

| Ratio DGH/DNBPA | Endpoint (ppm actives) | $\frac{Q_a}{Q_A} + \frac{Q_b}{Q_B}$ | Rating |
|---|---|---|---|
| 100/0 | 50 | 1.00 | |
| 0/100 | 5 | 1.00 | |
| 90/10 | 30 | 1.14 | Antagonistic |
| 10/90 | 5 | 0.91 | Synergistic |
| 75/25 | 20 | 1.30 | Antagonistic |
| 25/75 | 10 | 1.55 | Antagonistic |
| 50/50 | 40 | 4.4 | Antagonistic |

APPENDIX

Discussion

The conventional presentation of a test of synergy demands that the data be presented in terms of growth or no growth. The convention has the merit of presenting the data simply and directly in terms that make the calculation of synergy straightforward. This presentation may, however, require a thorough explanation of the factors which are taken into account in the determination of the endpoints of the test. The determination of synergy depends wholly on these endpoints.

The data presented in Table I demonstrate synergy, but may require explanation. First, the indication of growth (+) in Table I is heavy growth. No growth (−) indicates no growth on a zero-dilution plate, on a one-dilution plate, and on a two dilution plate. The zero-dilution plate will show as few as one bacterial colony per milliliter; the lowest count on one-dilution plate is ten bacteria per milliliter, and the two-dilution plate shows a bacterial count greater than $10^2$ bacteria per milliliter. In short, in Table I, the difference between growth (+) and no growth (−) involves a three-log reduction in bacterial count. For example, in the case of the ratio 100/0, the bacterial count at 40 ppm was greater than $10^2$ bacteria per milliliter. At 50 ppm, the bacterial count was below detection (less than 1 bacteria per milliliter). Therefore, the endpoint for 100/0 is taken to be 50 ppm.

The endpoint for 100/0 is, in the strictest sense, between 40 and 50 ppm. In this case, where a concentration of toxicant as high as 40 ppm is not capable of completely inhibiting growth, a three-log reduction in bacterial count is not to be expected where the concentration of biocide is increased by less than 5–10 ppm. The endpoint cannot fall closer to 40 ppm than to 50 ppm. The 10 ppm interval is indeed significant when testing toxicants with this magnitude of toxicity. Additional data points at closer intervals are unnecessary. The progression of the increments between concentrations in these experiments (0.3, 0.6, 1.0, 1.5, 3.0, 5.0, 7.5, 10, 20 ... etc.) is standard method in producing representative microbiological data.

The same logic applies to all the endpoints of the test. The best and worst extrapolations of the data can be determined in this way. Since the endpoints of 100/0 must fall closer to 50 than to 40 ppm, and the endpoint of 0/100 must fall closer to 5 than to 3 ppm, let us say that;

$45 < QA < 50$ $4 < QB < 5$ though it is very unlikely that the endpoints would occur at the lower concentrations. Let us use the ratio 50/50 in this example. For the reasons described above, the endpoint for 50/50 must fall closer to 5 than to 3, therefore;

$4 < 50/50 < 5$

In the worst possible case;

$QA = 45$ $QB = 4$

The worst endpoint for 50/50 under these circumstances is 5 ppm. Therefore, $Qa = 0.5 \times 5 = 2.5$ $Qb = 0.5 \times 5 = 2.5$ Using the previously defined formula for the calculation of synergy the following synergistic result is determined:

$Qa/QA + Qb/QB = 0.681$

This formula shows the extent to which the combination of the two toxicants creates a surprising increase in activity. When the synergy ratio is less than 1, the combination is truly synergistic instead of antagonistic or merely additive. In this experiment, calculating the worst possible case for the least effective ratio, the ratio is still extremely synergistic.

In the case where the ratio is 50/50, the endpoint is 5 ppm, which is the same as the endpoint for ISOTH alone. This does not mean that the combination is only equal in activity to the one component, ISOTH. The calculation of synergy proves this. The combination appears to require the same amount of toxicant to produce an endpoint, but within the combination, each toxicant is actually more active. The calculation of Qa and Qb takes this into account. If the components were not showing more activity when used together, the synergy ratio would be 1.

In the test of synergy against bacteria, the endpoints are clearly defined, and the increase in activity presented by the combinations are generally well within the defined limits of synergistic activity.

This presentation of the data goes to show how truly representative the endpoints are. The data, as presented and calculated in Table I, are not extrapolated into the best or worst cases. Instead, the data summarize the activity shown using a standard method. As mentioned above, this interpretation also depends on understanding that the difference between growth and no growth in the synergy study against bacteria involves a three-log reduction in bacterial count. These interpretations of the data confirm that the ratios of toxicants 90/10 through 27/75, result in an unexpected amelioration of toxicity. The ratio 10/90 is probably also synergistic.

The data presented in Table II establishes that biocide compositions of this invention are synergistic when used against fungi. The control contained a total count for molds of $1.0 \times 10^4$ and for yeasts of $1.5 \times 10^5$. This is an extremely high count of fungi. The results are presented in terms of growth or no growth, in much the same way as the bacteria are presented. A total kill of fungi is very difficult to achieve and represents excellent activity for the invention as it would be applied commercially.

Unlike the test against bacteria, the synergy study against fungi cannot be interpreted in terms of best or worst cases. The nature of the growth and inhibition of yeasts in particular molds does not lend itself to interpretation of variations. The endpoints, as presented in terms of growth or no growth, are clearly defined. Small variations in concentrations of toxicants (2-3 ppm) will not affect the results. Any interpretation of the data for fungi confirm that all ratios of toxicants, 90/10 through 10/90, result in an unexpected amelioration of toxicity.

As the invention will be applied commercially, the entire range of weight ratios will be very important. Since may process waters tend to include various mixes of these common molds, yeasts and bacteria, many different ratios will be used to provide the best control of these microorganisms with the least amount of toxicant. This more effective use of toxicants is not only of commercial interest, but also of environmental interest.

| Calculations for Table I | |
|---|---|
| $Q_A = 50$ ppm active DGH | $\frac{Q_a}{Q_A} + \frac{Q_b}{Q_B} < 1 =$ Synergy |
| $Q_B = 5$ ppm active ISOTH | |
| A. 90/10 | B. 10/90 |
| $Q_a = 10$ ppm $\times$ .90 = 9 | $Q_a = 5$ ppm $\times$ .10 = .5 |
| $Q_b = 10$ ppm $\times$ .10 = 1 | $Q_b = 5$ ppm $\times$ .90 = 4.5 |
| $\frac{9}{50} + \frac{1}{5} = 0.380$ | $\frac{.5}{50} + \frac{4.5}{7.5} = 0.910$ |
| C. 75/25 | D. 25/75 |
| $Q_a = 7.5$ ppm $\times$ 0.75 = 5.625 | $Q_a = 5$ ppm $\times$ 0.25 = 1.25 |
| $Q_b = 7.5$ ppm $\times$ 0.25 = 1.875 | $Q_b = 5$ ppm $\times$ 0.75 = 3.75 |
| $\frac{5.625}{50} + \frac{1.875}{5} = 0.488$ | $\frac{1.25}{50} + \frac{3.75}{5} = 0.775$ |
| E. 50/50 | |
| $Q_a = 5$ ppm $\times$ 0.50 = 2.5 | |
| $Q_b = 5$ ppm $\times$ 0.50 = 2.5 | |
| $\frac{2.5}{50} + \frac{2.5}{5} = 0.550$ | |

| Calculations for Table II | |
|---|---|
| $Q_A = 40$ ppm active DGH | $\frac{Q_a}{Q_A} + \frac{Q_b}{Q_B} < 1 =$ Synergy |
| $Q_B = 7.5$ ppm active ISOTH | |
| A. 90/10 | B. 10/90 |
| $Q_a = 10$ ppm $\times$ .90 = 9 | $Q_a = 5$ ppm $\times$ .10 = .5 |
| $Q_b = 10$ ppm $\times$ .10 = 1 | $Q_b = 5$ ppm $\times$ .90 = 4.5 |
| $\frac{9}{40} + \frac{1}{7.5} = 0.358$ | $\frac{.5}{40} + \frac{4.5}{7.5} = 0.613$ |
| C. 75/25 | D. 25/75 |
| $Q_a = 7.5$ ppm $\times$ 0.75 = 5.625 | $Q_a = 5$ ppm $\times$ 0.25 = 1.25 |
| $Q_b = 7.5$ ppm $\times$ 0.25 = 1.875 | $Q_b = 5$ ppm $\times$ 0.75 = 3.75 |
| $\frac{5.625}{40} + \frac{1.875}{7.5} = 0.391$ | $\frac{1.25}{40} + \frac{3.75}{7.5} = 0.531$ |
| E. 50/50 | |

| -continued | |
|---|---|
| Calculations for Table II | |
| $Q_a = 3$ ppm $\times$ 0.50 = 1.5 | |
| $Q_b = 3$ ppm $\times$ 0.50 = 1.5 | |
| $\frac{1.5}{40} + \frac{1.5}{7.5} = 0.238$ | |

Having thus described the invention, it is claimed as follows:

1. A synergistic biocidal composition useful in treating industrial process waters to prevent the growth of gram-negative bacteria and fungi which comprises from 10-90% by weight of dodecyl guanidine hydrochloride and from 90-10% by weight of a mixture comprising:
   (a) 5-chloro-2-methyl-4-isothiazolin-3-one and
   (b) 2-methyl-4-isothiazolin-3-one with the weight ratio of (a) to (b) being 1.15 to 0.35.

2. The synergistic biocidal composition of claim 1, wherein the gram-negative bacteria is a Pseudomonas bacteria.

3. The synergistic biocidal composition of claim 1, wherein the fungi is selected from the group consisting of Saccharomyces yeast and Aspergillus mold.

4. The synergistic biocidal composition of claim 3 wherein the Saccharomyces yeast is *Saccharomyces cerevisiae* and the Aspergillus mold is *Aspergillus niger*.

5. A method of controlling the growth of gram-negative bacteria and fungi of the type commonly found in industrial process waters which comprises treating said waters with a bactericidal and fungicidal amount of the composition of claim 1.

6. A method for controlling the growth of Pseudomonas bacteria which comprises treating said waters with a bactericidal amount of the composition of claim 1.

7. A method for controlling the growth of fungi selected from the group consisting of Saccharomyces yeast and Aspergillus molds which comprises treating said waters with a fungicidal amount of the composition of claim 1.

8. A method for controlling the growth of gram-negative bacteria and fungi of the type commonly found in industrial process waters which comprises treating said waters with a bactericidal and fungicidal amount of the composition of claim 3.

9. The method of claim 8 comprising the dosing of industrial process water with from 1-10 ppm of a composition comprised of 10-90% by weight of dodecyl guanidine hydrochloride and from 90-10% by weight of a mixture comprising:
   (a) 5-chloro-2-methyl-4-isothiazolin-3-one and
   (b) 2-methyl-4-isothiazolin-3-one with the weight ratio of (a) to (b) being 1.15 to 0.35.

10. A synergistic biocidal composition useful in treating industrial process waters to prevent the growth of gram-negative bacteria which comprises from 90-25% by weight of dodecyl guanidine hydrochloride and from 10-75% by weight of a mixture comprising:
    (a) 5-chloro-2-methyl-4-isothiazolin-3-one and
    (b) 2-methyl-4-isothiazolin-3-one with the weight ratio of (a) to (b) being 1.15 to 0.35.

* * * * *

UNITED STATES PATENT AND TRADEMARK OFFICE
CERTIFICATE OF CORRECTION

PATENT NO. : 4,661,503
DATED : APRIL 28, 1987
INVENTOR(S) : CYNTHIA H. MARTIN & THOMAS M. LAMARRE

It is certified that error appears in the above-identified patent and that said Letters Patent is hereby corrected as shown below:

Front page, Title:

SYNERGISTIC BIOCIDE OF DODECYL GUANIDINE HYDROCHLORIDE AND A MIXTURE OF 5-CHLORO-2-METHYL-4-ISOTHIAZOLIN-3-ONE

Letters Patent Should Read As: Title:

SYNERGISTIC BIOCIDE OF DODECYL GUANIDINE HYDROCHLORIDE AND A MIXTURE OF 5-CHLORO-2-METHYL-4-ISOTHIAZOLIN-3-ONE AND 2-METHYL-4-ISOTHIAZOLIN-3-ONE

Signed and Sealed this

Twenty-seventh Day of October, 1987

Attest:

DONALD J. QUIGG

Attesting Officer

Commissioner of Patents and Trademarks